(12) United States Patent
Lee et al.

(10) Patent No.: US 10,088,453 B2
(45) Date of Patent: Oct. 2, 2018

(54) APPARATUS AND METHOD OF DETECTING DEFECT OF STEEL PLATE

(71) Applicant: POSCO, Pohang-si, Gyeongsangbuk-do (KR)

(72) Inventors: Ju-Seung Lee, Pohang-si (KR); Chang-Hyun Park, Pohang-si (KR); Geon Shin, Pohang-si (KR); Sang-Woo Choi, Pohang-si (KR); Shin-Hwan Kang, Gwangyang-si (KR); Ho-Moon Bae, Pohang-si (KR); Ki-Jang Oh, Pohang-si (KR)

(73) Assignee: POSCO, Pohang-si, Gyeongsangbuk-do (KR)

( * ) Notice: Subject to any disclaimer, the term of this patent is extended or adjusted under 35 U.S.C. 154(b) by 127 days.

(21) Appl. No.: 15/102,506

(22) PCT Filed: Dec. 24, 2013

(86) PCT No.: PCT/KR2013/012076
§ 371 (c)(1),
(2) Date: Jun. 7, 2016

(87) PCT Pub. No.: WO2015/088089
PCT Pub. Date: Jun. 18, 2015

(65) Prior Publication Data
US 2016/0313285 A1    Oct. 27, 2016

(30) Foreign Application Priority Data

Dec. 11, 2013 (KR) .................. 10-2013-0154036

(51) Int. Cl.
*G01N 27/82* (2006.01)

(52) U.S. Cl.
CPC .................... *G01N 27/82* (2013.01)

(58) Field of Classification Search
CPC ........................................ G01N 27/82
See application file for complete search history.

(56) References Cited

U.S. PATENT DOCUMENTS 4,510,447 A    4/1985  Moyer
6,492,808 B1  12/2002  Sukhorukov et al.
(Continued)

FOREIGN PATENT DOCUMENTS

EP    0736173 A1   10/1996
EP    2940464 A1   11/2015
(Continued)

OTHER PUBLICATIONS

Extended European Search Report dated Nov. 21, 2016 issued in European Patent Applicaton No. 13899072.6.
(Continued)

*Primary Examiner* — Jermele M Hollington
*Assistant Examiner* — Feba Pothen
(74) *Attorney, Agent, or Firm* — McDermott Will & Emery LLP

(57) ABSTRACT

An aspect of the present disclosure may provide a defect detection apparatus and method for a steel plate, in which a defect in a steel plate may be detected, and particularly, only an inner defect in the steel plate may be detected, even with a relatively low amplification rate.

16 Claims, 6 Drawing Sheets

(56) References Cited

U.S. PATENT DOCUMENTS

| | | | | |
|---|---|---|---|---|
| 8,816,681 B2* | 8/2014 | Braun | ................... | G01N 27/87 324/228 |
| 2008/0042645 A1* | 2/2008 | Kaack | ................... | G01N 27/87 324/220 |
| 2009/0302835 A1* | 12/2009 | Sun | ................... | G01N 27/82 324/240 |
| 2014/0347041 A1 | 11/2014 | Lee et al. | | |
| 2015/0316508 A1 | 11/2015 | Lee et al. | | |

FOREIGN PATENT DOCUMENTS

| | | |
|---|---|---|
| JP | S63-221239 A | 9/1988 |
| JP | 05-312786 A | 11/1993 |
| JP | 5-322852 B2 | 12/1993 |
| JP | H07-63699 A | 3/1995 |
| JP | 2000-227419 A | 8/2000 |
| JP | 2001-194344 A | 7/2001 |
| JP | 2002-0060681 A | 2/2002 |
| JP | 2004-037216 A | 2/2004 |
| JP | 2004-037217 A | 2/2004 |
| JP | 2011-007565 A | 1/2011 |
| JP | 6060278 B2 | 1/2017 |
| KR | 2002-0060681 A | 7/2002 |
| KR | 10-2010-0076838 A | 7/2010 |
| KR | 10-2011-0025282 A | 3/2011 |
| KR | 10-2013-0068295 A | 6/2013 |
| WO | 95/018371 A1 | 7/1995 |
| WO | 2012/020932 A2 | 2/2012 |
| WO | 2013/089373 A1 | 6/2013 |

OTHER PUBLICATIONS

International Search Report dated Aug. 14, 2014 issued in International Patent Application No. PCT/KR2013/012076 (English translation).

Japanese Office Action dated Jun. 20, 2017 issued in Japanese Patent Application No. 2016-538612 (with English translation).

* cited by examiner

[FIG. 1]
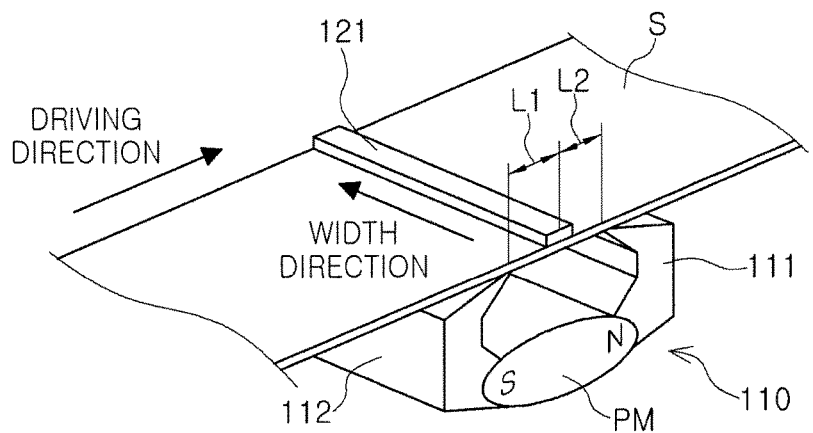
[FIG. 2]
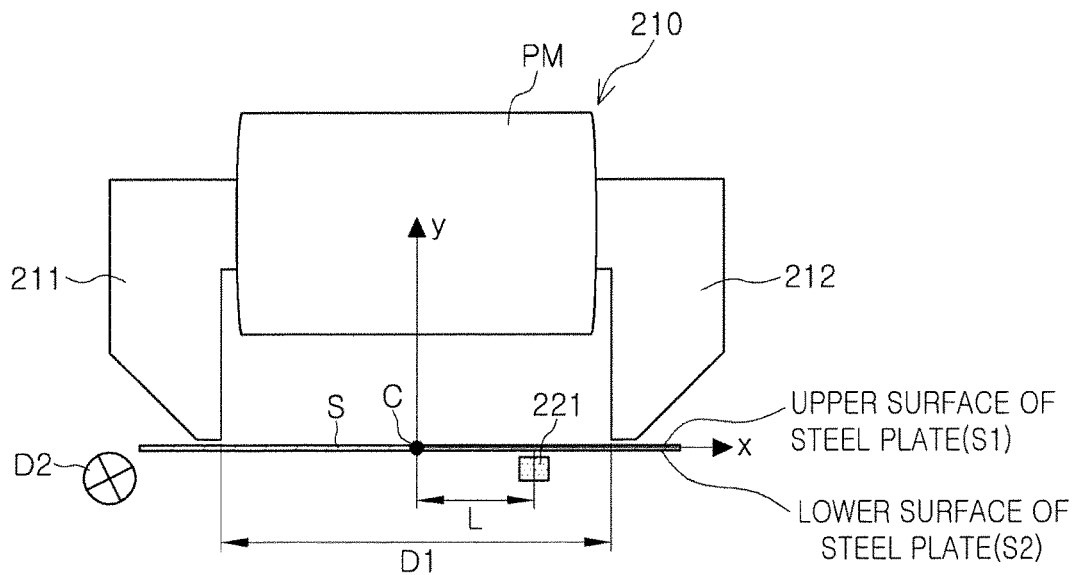

[FIG. 3]
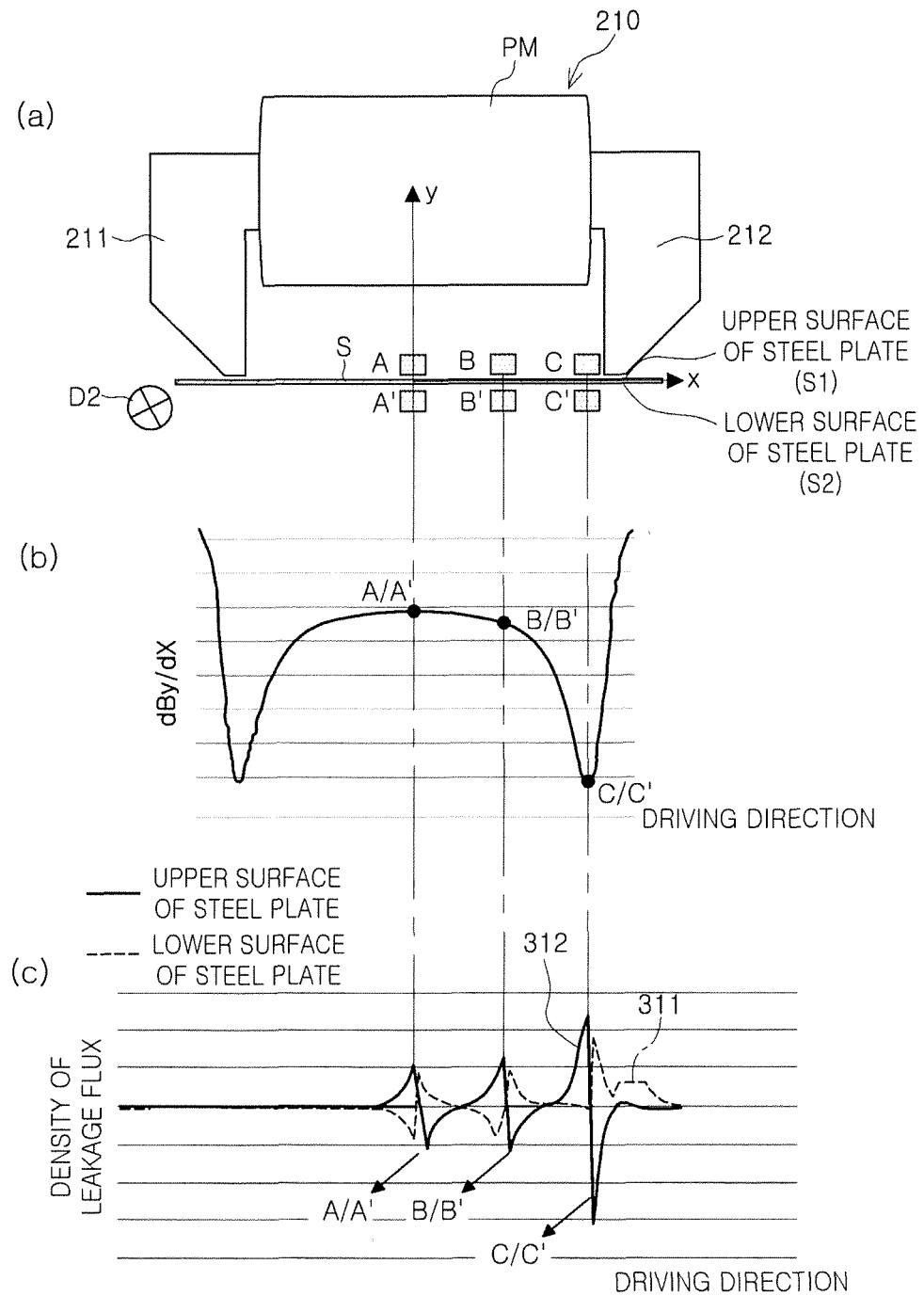

[FIG. 4]
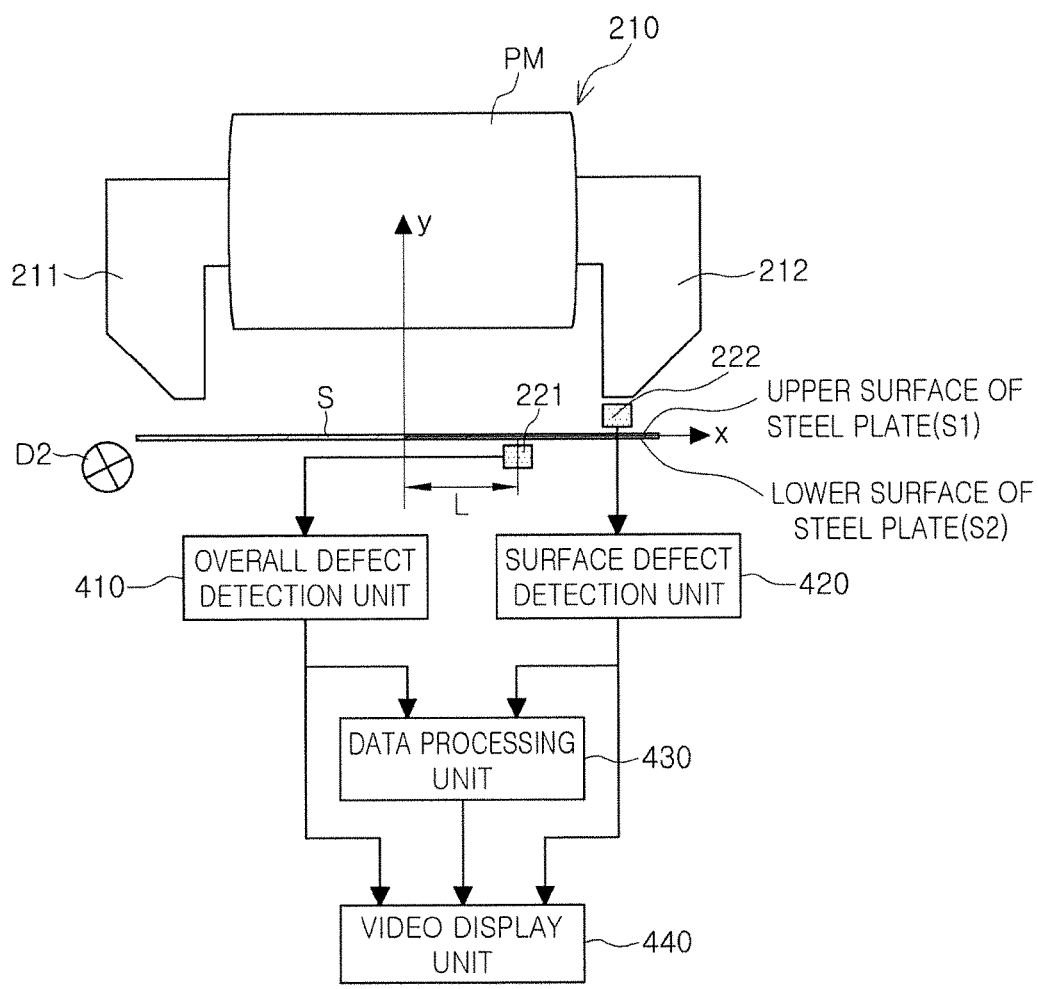

[FIG. 5]
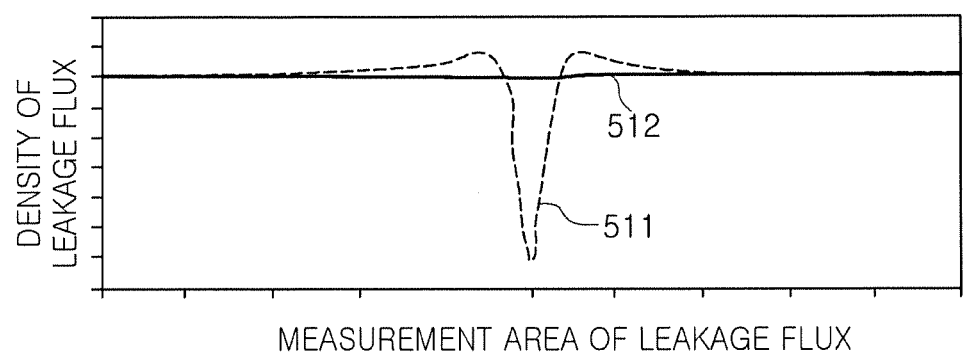

[FIG. 6]
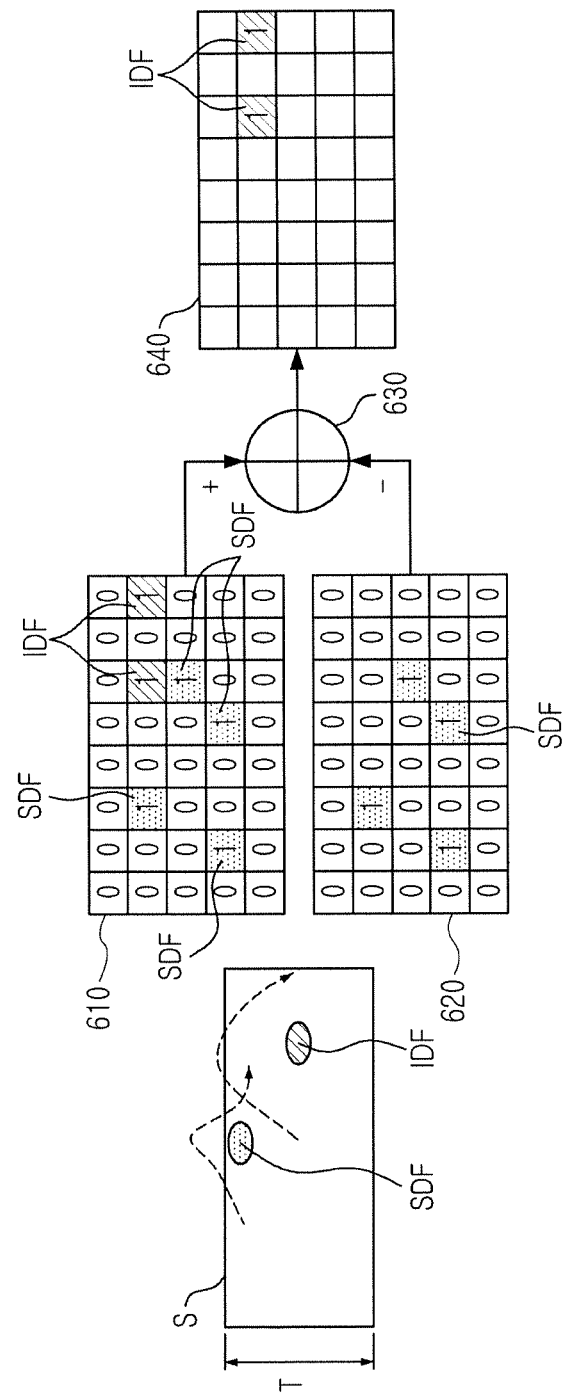

[FIG. 7]
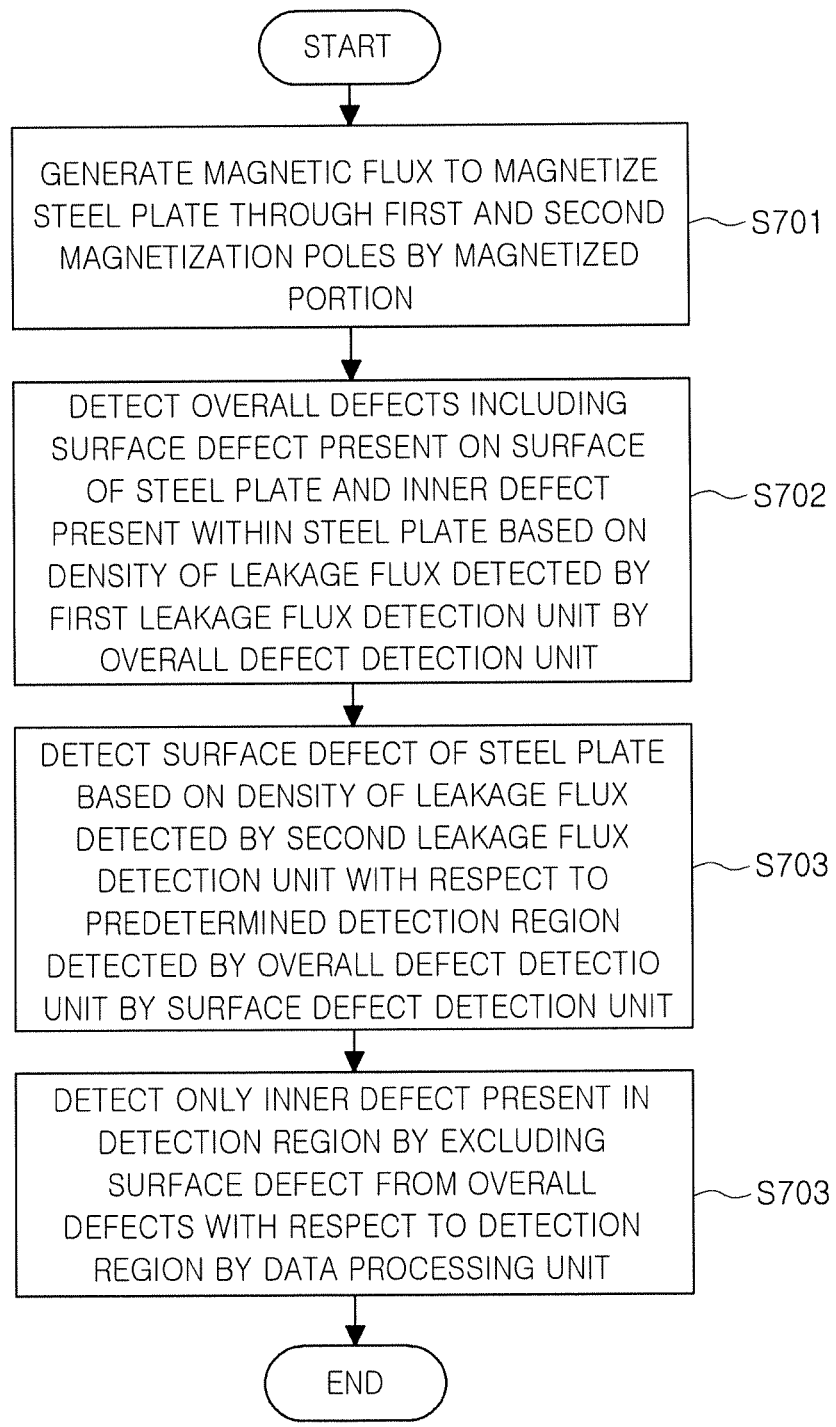

US 10,088,453 B2

APPARATUS AND METHOD OF DETECTING DEFECT OF STEEL PLATE

RELATED APPLICATIONS

This application is the U.S. National Phase under 35 U.S.C. § 371 of International Application No. PCT/KR2013/012076, filed on Dec. 24, 2013, which in turn claims the benefit of Korean Patent Application No. 10-2013-0154036 filed on Dec. 11, 2013, the disclosure of which applications are incorporated by reference herein.

TECHNICAL FIELD

The present disclosure relates to defect detection in a steel plate.

BACKGROUND ART

Techniques for detecting defects in a steel plate include an ultrasonic test method, a leakage flux inspection method, a magnetic particle inspection method, an eddy-current inspection method, an optical method, and the like.

The leakage flux inspection method is a technique to detect a defect in a steel plate based on leakage flux measured after the density of magnetic flux leaking externally from a surface of a steel plate due to a defect is detected using a magnetic sensor, such as a hall device, converting magnetic flux into an electrical signal.

In FIG. 1, a defect detection apparatus for a steel plate utilizing the foregoing leakage flux inspection method is illustrated.

As illustrated in FIG. 1, defect detection apparatuses for a steel plate of the related art may include a magnetized portion 110 generating magnetic flux to magnetize a steel plate S in a driving direction of the steel plate S and a magnetic sensor array 121 disposed in a width direction of the steel plate S and detecting the density of magnetic flux leaking when created magnetic flux passes through a defect in the steel plate S.

In the meantime, a magnetized portion 210 may include a permanent magnet PM and first and second magnetization poles 111 and 112 extending from opposing sides of the permanent magnet PM. In addition, the magnetic sensor array 121 may be disposed above the first and second magnetization poles 111 and 112 to be centered therebetween (in other words, to allow a distance L1 and a distance L2 to be equal to each other). Leakage flux measured by the magnetic sensor array 121 may be amplified to a predetermined density to be used in detecting a defect in the steel plate S.

In general, the density of leakage flux caused by a defect in the steel plate S may be lowest at the center between the first and second magnetization poles 111 and 112. Conversely, as a defect included in the driving steel plate S approaches the first and second magnetization poles 111 and 112, the density of leakage flux becomes increasingly higher. Thus, in a manner the same as the foregoing apparatus of the related art, in a case in which the magnetic sensor array 121 is disposed at the center between the first and second magnetization poles 111 and 112, there may be a problem in which an amplification rate of leakage flux measured by the magnetic sensor array 121 is required to be increased.

Furthermore, overall defects present not only on a surface of the steel plate S, but also present therewithin are included in leakage flux measured by the magnetic sensor array 121 disposed in the foregoing structure. Thus, there is a problem in which an inner defect present within the steel plate S may not be detected, separately.

Patent Document 1: Korean Patent Laid-Open Publication No. 2013-0068295 (Publication Date: Jun. 26, 2013).

DISCLOSURE

Technical Problem

An aspect of the present disclosure may provide a defect detection apparatus and method for a steel plate, in which a defect in a steel plate may be detected, and particularly, only an inner defect in the steel plate may be detected, even with a relatively low amplification rate.

Technical Solution

According to a first aspect of the present disclosure, a defect detection apparatus for a steel plate may include a magnetized portion generating magnetic flux to magnetize a steel plate through first and second magnetization poles and a leakage flux detection unit detecting a density of leakage flux leaking when the generated magnetic flux passes through a defect. In addition, the leakage flux detection unit may include a first leakage flux detection unit disposed to be spaced apart from a central position below and between the first and second magnetization poles in a driving direction of the steel plate or in a direction opposite to the driving direction, and disposed in a position in which a surface of the steel plate, opposing a surface of the steel plate above which the magnetized portion is provided, is provided, between two opposing surfaces of the steel plate, and may include a second leakage flux detection unit disposed below at least one of the first magnetization pole or the second magnetization pole while being disposed in a position of a surface of the steel plate in which the magnetized portion is provided, between the two opposing surfaces of the steel plate.

According to an aspect of the present disclosure, the defect detection apparatus for a steel plate may only detect an inner defect in the steel plate, based on a density of leakage flux detected by the first leakage flux detection unit and a density of leakage flux detected by the second leakage flux detection unit.

The first leakage flux detection unit may be disposed in a position in which an absolute value of a differential value of a magnetic flux component in a direction perpendicular to the steel plate with respect to the driving direction of the steel plate is the greatest, in the magnetic flux generated by the magnetized portion.

According to an aspect of the present disclosure, the defect detection apparatus for a steel plate may include an overall defect detection unit detecting overall defects including a surface defect present on the surface of the steel plate and an inner defect present within the steel plate, based on the density of leakage flux detected by the first leakage flux detection unit, and may further include a surface defect detection unit detecting a surface defect of the steel plate, based on the density of leakage flux detected by the second leakage flux detection unit, with respect to a predetermined detection region detected by the overall defect detection unit.

The defect detection apparatus for a steel plate may further include a data processing unit only detecting the inner defect present in the detection region by excluding the surface defect detected by the surface defect detection unit from the overall defects detected by the overall defect detection unit, with respect to the detection region.

The defect detection apparatus for a steel plate may further include a video display unit displaying at least one of the overall defects, the surface defect, and the inner defect, with respect to the detection region.

The overall defect detection unit may further provide first defect data regarding a position in which the detected overall defects are disposed in the detection region. In addition, the surface defect detection unit may further provide second defect data regarding a position in which the detected surface defect is disposed in the detection region. Furthermore, the data processing unit may only detect the inner defect present in the detection region by subtracting the provided second defect data from the provided first defect data.

The first defect data may be data representing a region in which the overall defects are present as a binary number "1" and a region in which the overall defects are not present as a binary number "0", in the detection region. In addition, the second defect data may be data representing a region in which the surface defect is present as a binary number "1" and a region in which the surface defect is not present as a binary number "0", in the detection region.

The leakage flux detection unit may include at least one of a hall sensor, a magnetoresistive sensor (MR sensor), a giant magnetoresistive sensor (GMR sensor), and a giant magnetoimpedance sensor (GMI sensor).

The leakage flux detection unit may be provided as a plurality of leakage flux detection units disposed in a width direction of the steel plate.

According to a second aspect of the present disclosure, a defect detection method for a steel plate may include a first step of generating magnetic flux, by a magnetized portion, to magnetize a steel plate through first and second magnetization poles; a second step of detecting, by an overall defect detection unit, overall defects including a surface defect present on a surface of the steel plate and an inner defect present within the steel plate, based on a density of leakage flux detected by a first leakage flux detection unit; a third step of detecting a surface defect of the steel plate, by a surface defect detection unit, based on the density of leakage flux detected by a second leakage flux detection unit, with respect to a predetermined detection region detected by the overall defect detection unit; and a fourth step of detecting only the inner defect present in the detection region by excluding the surface defect from the overall defects, with respect to the detection region.

The defect detection method for a steel plate may further include displaying at least one of the overall defects, the surface defect, or the inner defect, with respect to the detection region, by a video display unit.

The first leakage flux detection unit may be disposed to be spaced apart from a central position below and between the first and second magnetization poles in a driving direction of the steel plate or in a direction opposite to the driving direction and disposed in a position in which a surface of the steel plate, opposing a surface of the steel plate above which the magnetized portion is provided, is provided, between two opposing surfaces of the steel plate; and the second leakage flux detection unit may be disposed below and between the first and second magnetization poles and disposed in a position of a surface of the steel plate in which the magnetized portion is provided, between the two opposing surfaces of the steel plate.

The first leakage flux detection unit may be disposed in a position in which an absolute value of a differential value of a magnetic flux component in a direction perpendicular to the steel plate with respect to a driving direction of the steel plate is the greatest, in the magnetic flux generated by the magnetized portion.

In the second step, a first defect data regarding a region in which the detected overall defects are disposed in the detection region may be provided; in the third step, a second defect data regarding a region in which the detected surface defect is disposed in the detection region may be provided, and in the fourth step, only the inner defect present in the detection region may be detected by subtracting the provided second defect data from the provided first defect data.

The first defect data may be data representing the region in which the overall defects are present as a binary number "1" and the region in which the overall defects are not present as a binary number "0", in the detection region. In addition, the second defect data may be data representing the region in which the surface defect is present as a binary number "1" and the region in which the surface defect is not present as a binary number "0", in the detection region.

The first leakage flux detection unit or the second leakage flux detection unit may include at least one of a hall sensor, a magnetoresistive sensor (MR sensor), a giant magnetoresistive sensor (GMR sensor), and a giant magnetoimpedance sensor (GMI sensor).

The first leakage flux detection units or the second leakage flux detection units may be provided as a plurality of leakage flux detection units disposed in a width direction of the steel plate.

Advantageous Effects

According to an exemplary embodiment in the present disclosure, a defect in a steel plate may be detected even with a relatively low amplification rate by allowing a leakage flux detection unit to be disposed to be spaced apart from a central position below and between the first and second magnetization poles toward the magnetization pole by a predetermined distance.

Furthermore, according to another exemplary embodiment in the present disclosure, only an inner defect in a steel plate may be detected by excluding a surface defect of the steel plate, detected through a second leakage flux detection unit disposed below and between first and second magnetization poles from overall defects detected through a first leakage flux detection unit disposed to be spaced apart from a central position below and between the first and second magnetization poles by a predetermined distance.

DESCRIPTION OF DRAWINGS

FIG. 1 is a view illustrating a configuration of a defect detection apparatus for a steel plate of the related art.

FIG. 2 is a view illustrating a defect detection apparatus for a steel plate according to an exemplary embodiment in the present disclosure, taken in a width direction of a steel plate.

FIG. 3 is views illustrating differential values of component Y of magnetic flux and leakage flux densities depending on a position of a leakage flux detection unit.

FIG. 4 is a view illustrating a defect detection apparatus for a steel plate including a first leakage flux detection unit, taken in a width direction of a steel plate, according to another exemplary embodiment in the present disclosure.

FIG. 5 is a view illustrating the density of leakage flux caused by a defect present on a surface of a steel plate in a case in which a leakage flux detection unit is disposed below a magnetization pole.

FIG. 6 is a view illustrating a process in which a data processing unit in FIG. 4 only detects an inner defect.

FIG. 7 is a flowchart illustrating a defect detection method for a steel plate according to an exemplary embodiment in the present disclosure.

BEST MODE FOR INVENTION

Hereinafter, exemplary embodiments in the present disclosure will be described in detail with reference to the accompanying drawings. The disclosure may, however, be embodied in many different forms and should not be construed as being limited to the embodiments set forth herein. Rather, these embodiments are provided so that this disclosure will be thorough and complete, and will fully convey the scope of the disclosure to those skilled in the art. In the drawings, the shapes and dimensions of elements may be exaggerated for clarity, and the same reference numerals will be used throughout to designate the same or like elements.

FIG. 2 is a view illustrating a defect detection apparatus for a steel plate, taken in a width direction D2 of a steel plate, according to an exemplary embodiment in the present disclosure.

With reference to FIG. 2, a magnetized portion 210 may generate magnetic flux to magnetize a steel plate S in a driving direction (X direction) of the steel plate S, and may include a permanent magnet PM and first and second magnetization poles 211 and 212, yokes extending from two sides of the permanent magnet PM. A distance between the magnetization pole 211 and the second magnetization pole 212 is represented as D1, and the foregoing permanent magnet PM may be substituted with an electromagnet using a coil.

In addition, a first leakage flux detection unit 221 may be a magnetic sensor array to detect a density of leakage flux leaking when magnetic flux generated by the magnetized portion 210 passes through a defect in a steel plate S.

According to an exemplary embodiment in the present disclosure, as illustrated in FIG. 2, the first leakage flux detection unit 221 may be disposed below and between the first and second magnetization poles 211 and 212 to be spaced apart from a central position C below and between the first and second magnetization poles 211 and 212 by a predetermined distance L in a driving direction (X direction) of the steel plate S or in a direction opposite thereto, and may be disposed in a position in which a surface S2 of the steel plate is provided, the surface S2 being opposed to a surface S1 of the steel plate above which the magnetized portion 210 is disposed, between two surfaces S1 and S2 of the steel plate S.

According to an exemplary embodiment in the present disclosure, a position of the first leakage flux detection unit 221 in which it is spaced apart from the central position C by the predetermined distance L may correspond to a position in which an absolute value of a differential value of a magnetic flux component in a direction perpendicular to the driving direction (X direction) of the steel plate S, in magnetic flux generated by the magnetized portion 210, is the greatest (described later with reference to FIG. 3).

By allowing the first leakage flux detection unit 221 to be disposed in the position as described above, a defect in a steel plate may be detected with a relatively low amplification rate. A detailed description thereof will be described with reference to FIG. 3.

FIG. 3 are views illustrating a differential value of component Y of magnetic flux and a density of leakage flux depending on a position of a first leakage flux detection unit.

(a) of FIG. 3 illustrates positions of first leakage flux detection units, (b) of FIG. 3 illustrates differential values of component Y of magnetic flux in a direction perpendicular to a driving direction of a steel plate, depending on positions of the first leakage flux detection units, and (c) of FIG. 3 illustrates the density of leakage flux depending on positions of the first leakage flux detection units. In FIGS. 3, A, B, and C indicate second leakage flux detection units 222 disposed in a position in which a surface S1 of a steel plate and the magnetized portion 210 are provided, based on the steel plate S. In addition, A', B', and C' indicate first leakage flux detection units 221 disposed in a position in which a surface S2 of the steel plate is provided, based on the steel plate S, the surface S2 being opposed to the surface S1 above which the magnetized portion 210 is provided.

As illustrated in (b) of FIG. 3, in the case of a differential value dBy/dX of component Y of magnetic flux generated by the magnetized portion 210 with respect to a driving direction (X direction) of the steel plate S, it can be confirmed that differential values thereof are gradually increased from a central position A/A' below and between first and second magnetization poles 211 and 212 to a predetermined point C/C' in the driving direction (X direction) of the steel plate S.

As illustrated in (c) of FIG. 3, in a case in which a defect (including a surface defect and an inner defect) is present in the steel plate S, it can be confirmed that a density of detected leakage flux is also gradually increased from the central position A/A' below and between the first and second magnetization poles 211 and 212 to the predetermined point C/C' in the driving direction (X direction) of the steel plate S. However, it can be confirmed that a leakage flux density 312 of cases (A', B', and C') in which the first leakage flux detection units 221 are disposed below the lower surface S2 of the steel plate S (in other words, in a position in which the surface S2 of the steel plate S is provided, the surface S2 being opposed to a the surface S1 of the steel plate above which the magnetized portion 210 is provided, between the opposing surfaces S1 and S2 of the steel plate S) is higher than a leakage flux density 311 of cases (A, B, and C) in which the second leakage flux detection unit 222 is disposed above the upper surface S1 of the steel plate S (in other words, in a position in which the surface S1 of the steel plate and the magnetized portion 210 are provided, between the two opposing surfaces S1 and S2 of the steel plate S).

Thus, according to an exemplary embodiment, the first leakage flux detection unit (221 in FIG. 2) may be disposed to be spaced apart from the central position (C in FIG. 2) below and between the first and second magnetization poles 211 and 212 by a predetermined distance (L in FIG. 2) in the driving direction of the steel plate S or in the direction opposite thereto, and may be disposed in a position in which the surface S2 of the steel plate S is provided, the surface S2 being opposed to the surface S1 of the steel plate S above which the magnetized portion 210 is provided, between the two opposing surfaces S1 and S2 of the steel plate S. In addition, a position of the first leakage flux detection unit 221 in which it is spaced apart from the central position C by the predetermined distance (L in FIG. 2) may correspond to a position in which the absolute value of the differential value dBy/dX of the magnetic flux component in a direction perpendicular to the steel plate with respect to the driving direction (X direction) of the steel plate S, in magnetic flux generated by the magnetized portion 210, is the greatest. Thereby, a defect in the steel plate S may be detected even with a relatively low amplification rate.

FIG. 4 is a view illustrating a defect detection apparatus for a steel plate including a first leakage flux detection unit, taken in a width direction of a steel plate, according to another exemplary embodiment in the present disclosure. In addition, FIG. 5 is a view illustrating a density of leakage flux caused by a defect present on a surface of the steel plate in a case in which a leakage flux detection unit is disposed below a magnetization pole, and FIG. 6 is a view illustrating a process in which a data processing unit in FIG. 4 only detects an inner defect.

According to an exemplary embodiment illustrated in FIG. 4, the defect detection apparatus for a steel plate may further include a second leakage flux detection unit 222, an overall defect detection unit 410, a surface defect detection unit 420, and a data processing unit 430, besides components illustrated in FIG. 2.

Hereinafter, with reference to FIGS. 4 to 6, a defect detection apparatus for a steel plate according to another exemplary embodiment in the present disclosure will be described in detail.

As illustrated in FIG. 4, the first leakage flux detection unit 221 may be a magnetic sensor array to detect a density of leakage flux leaking when magnetic flux generated by a magnetized portion 210 passes through a defect (a surface defect or an inner defect) of a steel plate S. Data regarding the density of detected leakage flux may be transferred to the overall defect detection unit 410.

As described above, the first leakage flux detection unit 221 may be disposed to be spaced apart from a central position C below and between first and second magnetization poles 211 and 212 by a predetermined distance L in a driving direction (X direction) of the steel plate S or in a direction opposite thereto, and may be disposed in a position in which a surface S2 of the steel plate S is provided, the surface S2 being opposed to a surface S1 of the steel plate S above which the magnetized portion 210 is provided, between two opposing surfaces S1 and S2 of the steel plate S. In addition, a position of the first leakage flux detection unit 221 in which it is spaced apart from the central position C by the predetermined distance L may correspond to a position in which an absolute value of a differential value of a magnetic flux component in a direction perpendicular to the steel plate S with respect to the driving direction (X direction) of the steel plate S is the greatest (described later with reference to FIG. 3).

The overall defect detection unit 410 may detect overall defects including a surface defect present on a surface of the steel plate S and an inner defect present within the steel plate S based on a density of leakage flux detected by the first leakage flux detection unit 221. In other words, in a case in which the leakage flux density is equal to or higher than a predetermined value, the overall defect detection unit 410 may determine that an inner defect or a surface defect is present in the steel plate S. The detected overall defects may be transferred to a data processing unit 430.

In addition, the overall defect detection unit 410 may further provide first defect data regarding a region in which detected overall defects are disposed in a detection region.

In other words, as illustrated in FIG. 6, the overall defect detection unit 410 may provide the data processing unit 430 with the first defect data regarding the region in which the overall defects (an inner defect (IDF) and a surface defect (SDF)) are disposed in a detection region 610. In this case, the first defect data may be data representing a region in which the overall defects (IDF and SDF) are present as a binary number "1" and a region in which the overall defects are not present as a binary number "0", in the detection region 610.

In the meantime, the second leakage flux detection unit 222 may be a magnetic sensor array to detect the density of leakage flux leaking when magnetic flux generated by the magnetized portion 210 passes through a defect in the steel plate S, in detail, through a surface defect. The density of detected leakage flux may be transferred to the surface defect detection unit 420.

According to an exemplary embodiment in the present disclosure, the foregoing second leakage flux detection unit 222 may be disposed below and between at least one of the first magnetization pole 211 or the second magnetization pole 212, and may be disposed in a position of the surface S1 of the steel plate S in which the magnetized portion 210 is provided, between the two opposing surfaces S1 and S2 of the steel plate S. In an exemplary embodiment, the second leakage flux detection unit 222 may be disposed in a position in which the surface S2 of the steel plate S is provided, the surface S2 being opposed to the surface S1 of the steel plate S above which the magnetized portion 210 is provided, between the two opposing surfaces S1 and S2 of the steel plate S.

The second leakage flux detection unit 222 may be disposed below and between the first magnetization pole 211 or the second magnetization pole 212, as magnetic flux is generated in a direction perpendicular to a width of the steel plate S (See Tin FIG. 6) below the first and second magnetization poles 211 and 212. In this case, as illustrated in FIG. 5, a density of leakage flux 511 generated by the surface defect (See the surface defect (SDF) in FIG. 6) is even higher than a density of leakage flux 512 generated by the inner defect (See the inner defect (IDF) in FIG. 6). Leakage flux detected in this case may be a magnetic flux component in a direction perpendicular to the steel plate S. However, according to an exemplary embodiment in the present disclosure, in a case in which the density of the magnetic flux component in a direction perpendicular to the steel plate S is so high that the density thereof goes beyond a detection range of the second leakage flux detection unit 222, a density of a horizontal component among components of leakage flux may be detected.

Next, the surface defect detection unit 420 may only detect the surface defect of the steel plate S based on the density of leakage flux detected by the second leakage flux detection unit 222 in a region (620 in FIG. 6) the same as a predetermined detection region detected by the overall defect detection unit 410. In other words, in a case in which the density of leakage flux is equal to or higher than a predetermined value, the surface defect detection unit 420 may determine that the surface defect is present on the steel plate S. The detected surface defect may be transferred to the data processing unit 430.

In addition, the surface defect detection unit 420 may further provide second defect data regarding a region in which the detected surface defect is disposed in the detection region.

In other words, as illustrated in FIG. 6, the surface defect detection unit 420 may provide the data processing unit 430 with the second defect data regarding a region in which the surface defect (SDF) is disposed in a detection region 620. In this case, the second defect data may be data representing a region in which the surface defect (SDF) is present as a binary number "1" and a region in which the surface defect (SDF) is not present as a binary number "0", in the detection region 620. In this case, the detection region 610 and the detection region 620 refer to the same region as each other in the steel plate S.

In the meantime, the data processing unit 430 may only detect the inner defect present in the detection region by excluding the surface defect detected by the surface defect detection unit 420 from the overall defects detected by the overall defect detection unit 410 in the detection region 620.

In detail, as illustrated in FIG. 6, the data processing unit 430 may only detect the inner defect (IDF) present in a detection region 640 by subtracting the second defect data in the detection region 620 transferred by the surface defect detection unit 420 from the first defect data in the detection unit 610 transferred by the overall defect detection unit 410 using a subtractor 630.

Although the detection regions 610, 620, and 640 have different reference numerals in FIG. 6, the detection regions refer to the same region on a surface of the steel plate S.

Finally, a video display unit 440 may display at least one of the overall defects, the surface defect, or the inner defect with respect to the detection region. The video display unit 440 may include a display device and the like.

The first leakage flux detection unit 221 and the second leakage flux detection unit 222 may include at least one of a hall sensor, a magnetoresistive sensor (MR sensor), a giant magnetoresistive sensor (GMR sensor), and a giant magnetoimpedance sensor (GMI sensor). Furthermore, the first leakage flux detection unit or the second leakage flux detection unit may be provided as a plurality of leakage flux detection units disposed in a width direction of the steel plate S.

As described above, according to an exemplary embodiment in the present disclosure, the defect in the steel plate may be detected even with a relatively low amplification rate by allowing the leakage flux detection unit to be disposed to be spaced apart from the central position below and between the first and second magnetization poles toward the magnetization pole by a predetermined distance.

Furthermore, according to another exemplary embodiment in the present disclosure, only the inner defect in the steel plate may be detected by excluding the surface defect of the steel plate, detected through the second leakage flux detection unit disposed below the first and second magnetization poles from the overall defects detected through the first leakage flux detection unit disposed to be spaced apart from the central position below and between the first and second magnetization poles by a predetermined distance.

FIG. 7 is a flowchart illustrating a defect detection method for a steel plate according to an exemplary embodiment in the present disclosure.

Hereinafter, with reference to FIGS. 2 to 7, a method of detecting an inner defect in a steel plate according to an exemplary embodiment will be described. However, in order to simplify the present disclosure, an overlapping description with the description of FIGS. 2 to 6 will be omitted.

First, with reference to FIGS. 2 to 7, a magnetized portion 210 may generate magnetic flux to magnetize a steel plate S in a driving direction (X direction) of the steel plate S (S701).

Next, an overall defect detection unit 410 may detect overall defects including a surface defect present on a surface of the steel plate S and an inner defect present within the steel plate S, based on a density of leakage flux detected by a first leakage flux detection unit 221 (S702). In other words, in a case in which the density of leakage flux is equal to or higher than a predetermined value, the overall defect detection unit 410 may determine that the inner defect or the surface defect is present in the steel plate S. The detected overall defects may be transferred to a data processing unit 430.

In this case, as illustrated in FIG. 2, the first leakage flux detection unit 221 may be disposed to be spaced apart from a central position C below and between first and second magnetization poles 211 and 212 by a predetermined distance L in a driving direction (X direction) of the steel plate S or in a direction opposite thereto, and may be disposed in a position in which a surface S2 of the steel plate S is provided, the surface S2 being opposed to a surface S1 of the steel plate S above which the magnetized portion 210 is disposed, between two opposing surfaces S1 and S2 of the steel plate S. In addition, a position of the first leakage flux detection unit 221 in which it is spaced apart from the central position C by the predetermined distance L may correspond to a position in which an absolute value of a differential value of a magnetic flux component in a direction perpendicular to the driving direction (X direction) of the steel plate S, in magnetic flux generated by the magnetized portion 210, is the greatest.

Next, the surface defect detection unit 420 may only detect the surface defect of the steel plate S, based on the density of leakage flux detected by a second leakage flux detection unit 222 in the same region as a predetermined detection region detected by the overall defect detection unit 410 (S703). In other words, in a case in which the density of leakage flux is equal to or higher than a predetermined value, the surface defect detection unit 420 may determine that the surface defect is present on the steel plate S. The detected surface defect may be transferred to the data processing unit 430.

In this case, the second leakage flux detection unit 222 may be disposed directly below the first magnetization pole 211 or the second magnetization pole 212, and may be disposed in a position of the surface S1 of the steel plate S in which the magnetized portion 210 is provided, between the two opposing surfaces S1 and S2 of the steel plate S. In an exemplary embodiment, the second leakage flux detection unit 222 may be disposed in a position in which the surface S2 of the steel plate S, the surface S2 being opposed to the surface S1 of the plate above which the magnetized portion 210 is disposed, between the two opposing surfaces S1 and S2 of the steel plate S.

Finally, the data processing unit 430 may only detect the inner defect present in the detection region by excluding the surface defect detected by the surface defect detection unit 420 from the overall defects detected by the overall defect detection unit 410 with respect to the detection region (S704).

As described above, according to an exemplary embodiment in the present disclosure, the defect in the steel plate may be detected even with a relatively low amplification rate by allowing the leakage flux detection unit to be disposed to be spaced apart from the central position below and between the first and second magnetization poles toward the magnetization pole by a predetermined distance.

Furthermore, according to another exemplary embodiment in the present disclosure, only the defect in the steel plate may be detected by excluding the surface defect of the steel plate, detected through the second leakage flux detection unit disposed below the first and second magnetization poles from the overall defects detected through the first leakage flux detection unit disposed to be spaced apart from the central position below and between the first and second magnetization poles by a predetermined distance.

While exemplary embodiments have been shown and described above, it will be apparent to those skilled in the art that modifications and variations could be made without departing from the scope of the present invention as defined by the appended claims.

The invention claimed is:

1. A defect detection apparatus for a steel plate comprising:
a magnetized portion generating magnetic flux to magnetize the steel plate through first and second magnetization poles; and
a leakage flux detection unit detecting a density of leakage flux leaking when the generated magnetic flux passes through a defect;
wherein the leakage flux detection unit includes:
a first leakage flux detection unit disposed to be spaced apart from a central position below and between the first and second magnetization poles in a driving direction of the steel plate or in a direction opposite to the driving direction, and disposed in a position in which a first surface of the steel plate, opposing a second surface of the steel plate above which the magnetized portion is provided, is provided, between the first and second surfaces of the steel plate; and
a second leakage flux detection unit disposed below at least one of the first magnetization pole or the second magnetization pole, and disposed in a position of the second surface of the steel plate in which the magnetized portion is provided, between the first and second surfaces of the steel plate,
wherein the first leakage flux detection unit is disposed in a position in which an absolute value of a differential value of a magnetic flux component in a direction perpendicular to the steel plate with respect to the driving direction of the steel plate is the greatest, in the magnetic flux generated by the magnetized portion.

2. The defect detection apparatus for a steel plate of claim 1, wherein the defect detection apparatus for a steel plate only detects an inner defect in the steel plate, based on a density of leakage flux detected by the first leakage flux detection unit and a density of leakage flux detected by the second leakage flux detection unit.

3. The defect detection apparatus for a steel plate of claim 1, further comprising an overall defect detection unit detecting overall defects including a surface defect present on the surface of the steel plate and an inner defect present within the steel plate, based on the density of leakage flux detected by the first leakage flux detection unit; and a surface defect detection unit detecting a surface defect of the steel plate based on the density of leakage flux detected by the second leakage flux detection unit with respect to a predetermined detection region detected by the overall defect detection unit.

4. The defect detection apparatus for a steel plate of claim 3, further comprising a data processing unit only detecting the inner defect present in the detection region by excluding the surface defect detected by the surface defect detection unit from the overall defects detected by the overall defect detection unit, with respect to the detection region.

5. The defect detection apparatus for a steel plate of claim 4, further comprising a video display unit displaying at least one of the overall defects, the surface defect, and the inner defect, with respect to the detection region.

6. The defect detection apparatus for a steel plate of claim 4, wherein the overall defect detection unit further provides first defect data regarding a position in which the detected overall defects are disposed in the detection region, the surface defect detection unit further provides second defect data regarding a position in which the detected surface defect is disposed in the detection region, and the data processing unit only detects the inner defect present in the detection region by subtracting the provided second defect data from the provided first defect data.

7. The defect detection apparatus for a steel plate of claim 6, wherein the first defect data is data representing a region in which the overall defects are present as a binary number "1" and a region in which the overall defects are not present as a binary number "0", in the detection region, and
the second defect data is data representing a region in which the surface defect is present as a binary number "1" and a region in which the surface defect is not present as a binary number "0", in the detection region.

8. The defect detection apparatus for a steel plate of claim 1, wherein the leakage flux detection unit includes at least one of a hall sensor, a magnetoresistive sensor (MR sensor), a giant magnetoresistive sensor (GMR sensor), and a giant magnetoimpedance sensor (GMI sensor).

9. The defect detection apparatus for a steel plate of claim 1, wherein the leakage flux detection unit is provided as a plurality of leakage flux detection units disposed in a width direction of the steel plate.

10. A defect detection method for a steel plate, comprising:
a first step of generating magnetic flux, by a magnetized portion, to magnetize the steel plate through first and second magnetization poles;
a second step of detecting, by an overall defect detection unit, overall defects including a surface defect present on a surface of the steel plate and an inner defect present within the steel plate, based on a density of leakage flux detected by a first leakage flux detection unit;
a third step of detecting a surface defect of the steel, by a surface defect detection unit, based on the density of leakage flux detected by a second leakage flux detection unit, with respect to a predetermined detection region detected by the overall defect detection unit; and
a fourth step of detecting only the inner defect present in the detection region by excluding the surface defect from the overall defects, with respect to the detection region,
wherein the first leakage flux detection unit is disposed in a position in which an absolute value of a differential value of a magnetic flux component in a direction perpendicular to the steel plate with respect to a driving direction of the steel plate is the greatest, in the magnetic flux generated by the magnetized portion.

11. The defect detection method for a steel plate of claim 10, further comprising displaying at least one of the overall defects, the surface defect, or the inner defect, with respect to the detection region, by a video display unit.

12. The defect detection method for a steel plate of claim 10, wherein the first leakage flux detection unit is disposed to be spaced apart from a central position below and between the first and second magnetization poles in a driving direction of the steel plate or in a direction opposite to the driving direction and disposed in a position in which a first surface of the steel plate, opposing a second surface of the steel plate above which the magnetized portion is provided, is provided, between the first and second surfaces of the steel plate, and
the second leakage flux detection unit is disposed below and between at least one of the first and second magnetization poles and disposed in a position of the second surface of the steel plate in which the magnetized portion is provided, between the first and second surfaces of the steel plate.

13. The defect detection method for a steel plate of claim 10, wherein in the second step a first defect data regarding a region in which the detected overall defects are disposed in the detection region is provided, the third step, a second defect data regarding a region in which the detected surface defect is disposed in the detection region is provided, and in the fourth step, only the inner defect present in the detection region is detected by subtracting the provided second defect data from the provided first defect data.

14. The defect detection method for a steel plate of claim 13, wherein the first defect data is data representing the region in which the overall defects are present as a binary number "1" and the region in which the overall defects are not present as a binary number "0", in the detection region and the second defect data is data representing the region in which the surface defect is present as a binary number "1" and the region in which the surface defect is not present as a binary number "0", in the detection region.

15. The defect detection method for a steel plate of claim 10, wherein the first leakage flux detection unit or the second leakage flux detection unit includes at least one of a hall sensor, a magnetoresistive sensor (MR sensor), a giant magnetoresistive sensor (GMR sensor), and a giant magnetoimpedance sensor (GMI sensor).

16. The defect detection method for a steel plate of claim 10, wherein the first leakage flux detection unit or the second leakage flux detection unit is provided as a plurality of leakage flux detection units disposed in a width direction of the steel plate.

* * * * *